United States Patent
Omotowa

(10) Patent No.: US 7,745,673 B2
(45) Date of Patent: Jun. 29, 2010

(54) PROCESSES FOR PRODUCING HYDROHALOCARBON AND HALOCARBON COMPOUNDS USING SILICON TETRAFLUORIDE

(75) Inventor: Bamidele Omotowa, Idaho Falls, ID (US)

(73) Assignee: International Isotopes Inc., Idaho Falls, ID (US)

( * ) Notice: Subject to any disclaimer, the term of this patent is extended or adjusted under 35 U.S.C. 154(b) by 0 days.

(21) Appl. No.: 12/203,654

(22) Filed: Sep. 3, 2008

(65) Prior Publication Data

US 2009/0069589 A1    Mar. 12, 2009

Related U.S. Application Data

(60) Provisional application No. 60/969,883, filed on Sep. 4, 2007.

(51) Int. Cl.
*C07C 19/08* (2006.01)
(52) U.S. Cl. .................................................. 570/134
(58) Field of Classification Search ........................ None
See application file for complete search history.

(56) References Cited

U.S. PATENT DOCUMENTS

| | | | |
|---|---|---|---|
| 1,973,069 A * | 9/1934 | Henne | 570/162 |
| 3,287,426 A * | 11/1966 | Christe et al. | 570/162 |
| 4,070,439 A | 1/1978 | Osaka et al. | |
| 4,876,406 A * | 10/1989 | Foulletier | 570/165 |
| 5,091,602 A | 2/1992 | Park et al. | |
| 5,399,549 A | 3/1995 | Felix et al. | |
| 5,399,796 A | 3/1995 | Correia et al. | |
| 5,446,216 A | 8/1995 | Rao | |
| 5,545,770 A | 8/1996 | Rao | |
| 5,831,136 A | 11/1998 | Rao | |
| 5,841,006 A | 11/1998 | Cuzzato et al. | |
| 5,918,106 A | 6/1999 | Bulko et al. | |
| 6,074,985 A | 6/2000 | Elsheikh et al. | |
| 6,127,586 A | 10/2000 | Scott et al. | |
| 6,229,058 B1 | 5/2001 | Sievert et al. | |
| 6,232,514 B1 | 5/2001 | Cuzzato et al. | |
| 6,268,541 B1 | 7/2001 | Kono et al. | |
| 6,392,106 B1 | 5/2002 | Kono et al. | |
| 6,433,233 B1 | 8/2002 | Kanemura et al. | |
| 6,479,718 B1 | 11/2002 | Elsheikh et al. | |
| 6,503,865 B1 | 1/2003 | Kanemura et al. | |
| 6,841,705 B2 | 1/2005 | Yuichi et al. | |
| 7,067,707 B2 | 6/2006 | Piepho et al. | |
| 7,071,368 B1 | 7/2006 | Merkel et al. | |
| 7,074,973 B2 | 7/2006 | Nappa et al. | |
| 2001/0049457 A1 | 12/2001 | Stephens | |
| 2008/0262274 A1 | 10/2008 | Omotowa | |
| 2008/0262275 A1 | 10/2008 | Omotowa | |
| 2008/0262276 A1 | 10/2008 | Omotowa | |
| 2008/0262277 A1 | 10/2008 | Omotowa | |

OTHER PUBLICATIONS

Christe et al., Journal of Organic Chemistry (1964), 29(10), 3007-9.*

(Continued)

*Primary Examiner*—Karl J Puttlitz
(74) *Attorney, Agent, or Firm*—Perkins Coie LLP

(57) ABSTRACT

Methods and systems for producing hydrohalocarbon and/or halocarbon compounds with an inorganic fluoride (e.g., silicon tetrafluoride ($SiF_4$)) are disclosed herein.

11 Claims, 4 Drawing Sheets

OTHER PUBLICATIONS

Office Action for U.S. Appl. No. 11/853,521; Mailed on Apr. 11, 2008, 7 pgs.
Office Action for U.S. Appl. No. 11/853,541; Mailed on Mar. 14, 2008, 8 pgs.
Office Action for U.S. Appl. No. 11/853,557; Mailed on Mar. 14, 2008, 8 pgs.
Office Action for U.S. Appl. No. 11/853,572; Mailed on Mar. 14, 2008, 8 pgs.
Okazaki et al., Kogyo Kagaku Zasshi, 72(3), 1969, pp. 630-633.
Park et al., Kongop Hwahak, 4(2), 1993, pp. 318-323.
Schumb, W.C., "Some Metathetical Reactions of the Gaseous Fluorides of Group IV," Journal of the American Chemical Society, vol. 74, Jun. 1951, pp. 1754-1760.
International Search Report and Written Opinion, International Application No. PCT/US08/75133, Applicant: International Isotopes, Inc., mailed Nov. 24, 2008, 10 pages.

* cited by examiner

PROCESSES FOR PRODUCING HYDROHALOCARBON AND HALOCARBON COMPOUNDS USING SILICON TETRAFLUORIDE

CROSS-REFERENCE TO RELATED APPLICATION(S)

This application claims the benefit of U.S. Provisional Application No. 60/969,883, entitled "PROCESSES FOR PRODUCING HYDROHALOCARBON AND HALOCARBON COMPOUNDS USING SILICON TETRAFLUORIDE," filed Sep. 4, 2007, which application is hereby incorporated by reference in its entirety.

TECHNICAL FIELD

The present disclosure is related to processes for producing hydrohalocarbon (e.g., hydrofluorocarbon) compounds and/or halocarbon compounds.

BACKGROUND

Chlorofluorocarbon (CFC) and hydrochlorofluorocarbon (HCFC) compounds have been used as refrigerants, fire extinguishing agents, propellants, and solvents since the early twentieth century. However, CFC and HCFC compounds are now believed to deplete the ozone layer of the earth via UV-promoted reactions. As a result, the U.S. Environmental Protection Agency has already banned the production and importation of certain products comprising CFC and HCFC compounds.

Internationally, the Montreal Protocol has set out plans for replacing CFC and HCFC compounds with hydrofluorocarbon (HFC) compounds. However, the cost of producing HFC compounds is considerably higher than that of producing CFC or HCFC compounds. Presently, industrial fluorination processes for producing HFC are based on hydrogen fluoride (HF) fluorination of chlorocarbons. FIG. 1 presents examples of known potential multistep routes to produce 1,1,2,2,2-pentafluoroethane (HFC-125) and 1,2,2,2-tetrafluoroethane (HFC-134a).

As illustrated in FIG. 1, multistep processes are typically required to produce HFC-125 from either 1,1,2-trichloroethene (triclene) or 1,1,2,2-tetrachloroethene (perclene). For example, HFC-125 can be produced by first converting either triclene or perclene into 1,1-dichloro-2,2,2-trifluoroethane (HCFC-123) and then fluorinating HCFC-123 to 2-chloro-1,1,1,2-tetrafluoroethane (HCFC-124). HFC-125 can then be produced by performing chlorine-fluorine exchange on HCFC-124 with hydrogen fluoride. Similarly, as illustrated in FIG. 1, HFC-134a can also be produced with either triclene or perclene using multistep processes.

The processes for producing HFC-125 and HFC-134a are more complex, both chemically and operationally, than those for CFC and HCFC compounds. Moreover, both the triclene and perclene-based processes require disposing of hydrogen chloride (HCl) byproducts. Procedures and equipment are available to convert some of the HCl byproducts into a chlorine ($Cl_2$) gas and subsequently recycle the chlorine gas back into the production process. Nonetheless, this recycling operation adds to the cost of the overall HFC production process. Therefore, there is a need to develop more efficient and cost-effective processes for producing HFC compounds, such as HFC-125 and HFC-134a.

DETAILED DESCRIPTION

Figure 1:
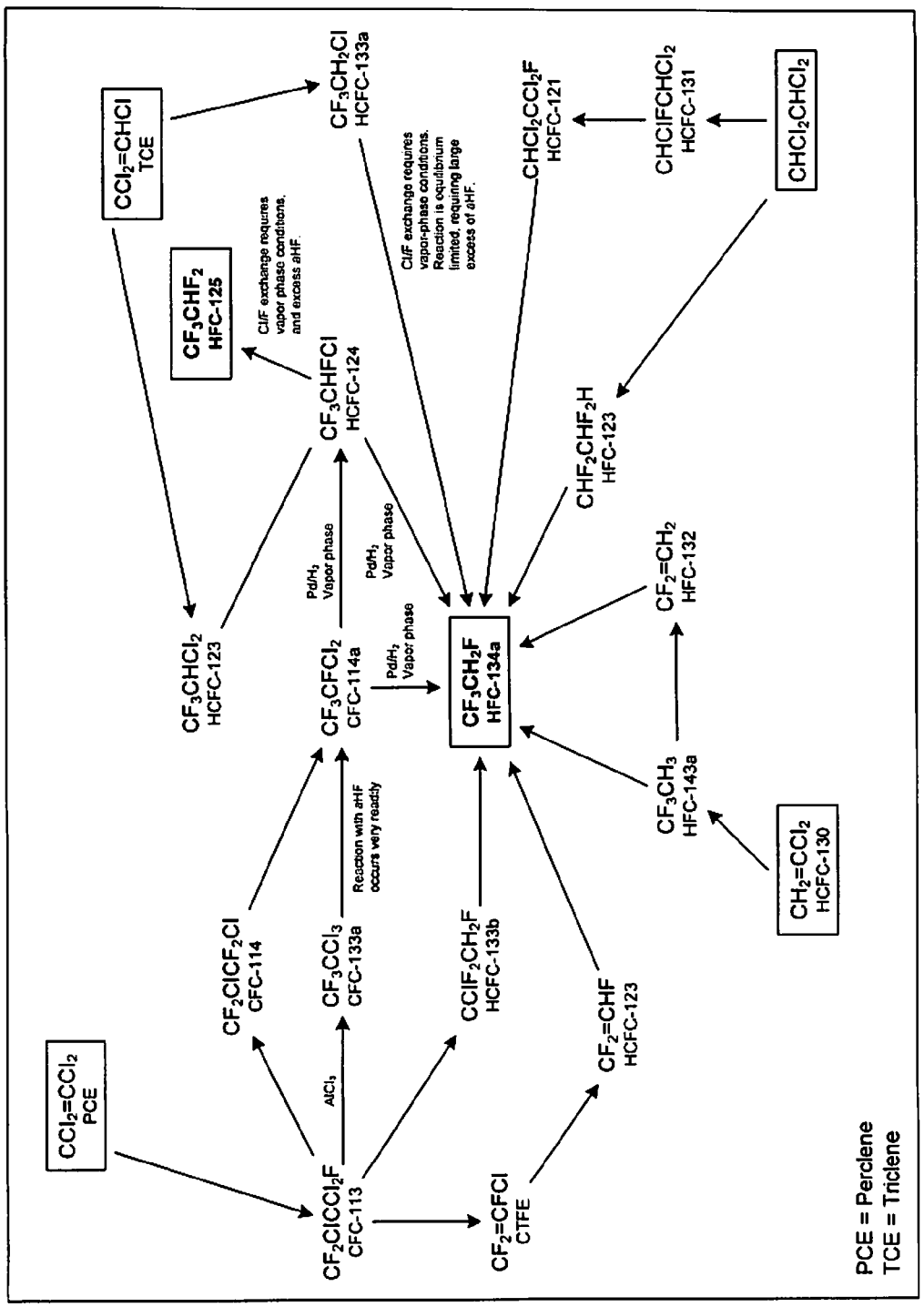
FIG. 1 is a schematic diagram illustrating potential routes to HFC-125 and HFC-134a in accordance with the prior art.

Specific details of several embodiments of the disclosure are described below with reference to processes for efficiently and cost-effectively producing hydrohalocarbon and/or halocarbon compounds. Hydrohalocarbon compounds generally refer to halogen-substituted (e.g., fluorine-, chlorine-, bromine-, and/or iodine-substituted) organic compounds containing carbon and hydrogen. Hydrohalocarbon compounds can include hydrofluorocarbon compounds containing fluorine, carbon, and hydrogen, hydrochlorocarbon compounds containing chlorine, carbon, and hydrogen, and hydrochlorofluorocarbon compounds containing fluorine, chlorine, carbon, and hydrogen. Halocarbon compounds generally refer to halogen-substituted organic compounds containing only carbon and halogen. For example, halocarbon compounds can include chlorofluorocarbon compounds containing only chlorine, fluorine, and carbon, chlorocarbon compounds containing only carbon and chlorine, and fluorocarbon compounds containing only carbon and fluorine. Several other embodiments of the invention may have different configurations, components, or procedures than those described in this section. A person of ordinary skill in the art, therefore, will accordingly understand that the invention may have other embodiments with additional elements, or the invention may have other embodiments without several of the elements shown and described below.

One aspect of the present disclosure is directed to the use of an inorganic fluoride as a fluorinating agent for producing HFC, CFC, and/or HCFC compounds. The following description uses $SiF_4$ as an example of an inorganic fluoride to show various embodiments of the fluorination reaction of the present disclosure for illustration purposes. However, a skilled artisan will appreciate that $SiF_4$ is merely an example of an inorganic fluoride. Other inorganic fluorides suitable for use in the systems and processes provided herein can include at least one of germanium tetrafluoride ($GeF_4$), bromine trifluoride ($BrF_3$), manganese tetrafluoride ($MnF_4$), sulfur tetrafluoride ($SF_4$), bromine pentafluoride ($BrF_5$), and tungsten hexafluoride ($WF_6$).

In one embodiment, the present disclosure relates to reacting $SiF_4$ with 1,1,2,2,2-pentachloroethane (referred to as pentachloroethane hereinafter) to produce at least one of 1,1,2,2-tetrachloro-1-fluoroethane (HCFC-121), 1,2,2-trichloro-1,2-difluoroethane (HCFC-122), HCFC-123, HCFC-124, and HFC-125. In another embodiment, the present disclosure relates to reacting $SiF_4$ with 1,1,1,2,2,2-hexachloroethane (referred to as hexachloroethane hereinafter) to produce at least one of 1,1,1,2,2-pentachloro-2-fluoroethane (CFC-111), 1,1,2,2-tetrachloro-1,2-difluoroethane (CFC-112), 1,1,2-trichloro-1,2,2-trifluoroethane (CFC-113), 1,2-dichloro-1,1,2,2-tetrafluoroethane (CFC-114), 1-chloro-1,1,2,2,2-pentafluoroethane (CFC-115), and/or other CFC compounds. In yet another embodiment, the present disclosure relates to reacting $SiF_4$ with 1,1,2,2-tetrachloroethane (referred to as tetrachloroethane hereinafter) to produce at least one of 1,1,1-trichloro-2-fluoroethane (HCFC-131b), 1,2,-dichloro-1,2-difluoroethane (HCFC-132a), 1-chloro-1,2,2-trifluoroethane (HCFC-133a), and 1,1,2,2-tetrafluoroethane (HFC-134). In a further embodiment, the present disclosure relates to reacting $SiF_4$ with 1,1,1-trichloroethane (referred to as trichloroethane hereinafter) to produce 1,1,1-trifluoroethane (HFC-143a). In further embodiments, the present disclosure relates to reacting $SiF_4$ with chlorine-substituted aromatic compounds, olefins, alcohols, carboxylic acids, esters, ethers, ketones, and/or aldehydes to produce HFC, CFC, and/or HCFC compounds.

A further aspect of the present disclosure is directed to using one or more catalysts to catalyze a fluorination reaction using an inorganic fluoride in the presence of a chlorocarbon compound and/or a hydrochlorocarbon compound. It is believed that, in certain embodiments, the class of compounds known as superacids and/or Lewis acids can catalyze such fluorination reactions. The term "superacid" generally refers to an acid with an acidity greater than that of 100% sulfuric acid ($H_2SO_4$). Examples of superacids include trifluoromethane sulfonic acid ($CF_3SO_3H$) and fluorosulfuric acid ($FSO_3H$). The term "Lewis acid" generally refers to a compound that is an electrophile or an electron acceptor. Examples of Lewis acids include aluminum trichloride ($AlCl_3$), iron trichloride ($FeCl_3$), boron trifluoride ($BCl_3$), niobium pentachloride ($NbCl_5$), and the lanthanide triflates, e.g., ytterbium(III) triflate. In certain embodiments, the catalyst can include aluminum trichloride ($AlCl_3$). The inventor believes that $AlCl_3$ can react with $SiF_4$ to form $AlCl_xF_y$, (x+y=3), in situ, which has been observed by the inventor to catalyze the $SiF_4$ fluorination of chlorocarbon and/or hydrohalocarbon compounds. In other embodiments, the catalyst can include antimony pentachloride ($SbCl_5$). In further embodiments, $SbCl_3$, $SbF_5$, $SbF_3$, $AsF_5$, $AsCl_3$, $TaCl_5$, $TaF_5$, $NbCl_5$, $NbF_5$, $HSO_3F$, $CF_3SO_3F$, $Cr_2O_3$, and/or other suitable inorganic halides can also be used to catalyze the fluorination of hydrohalocarbon and/or halocarbon compounds in the presence of an inorganic fluorinating agent, e.g., $SiF_4$.

Reaction Systems

Figure 2:
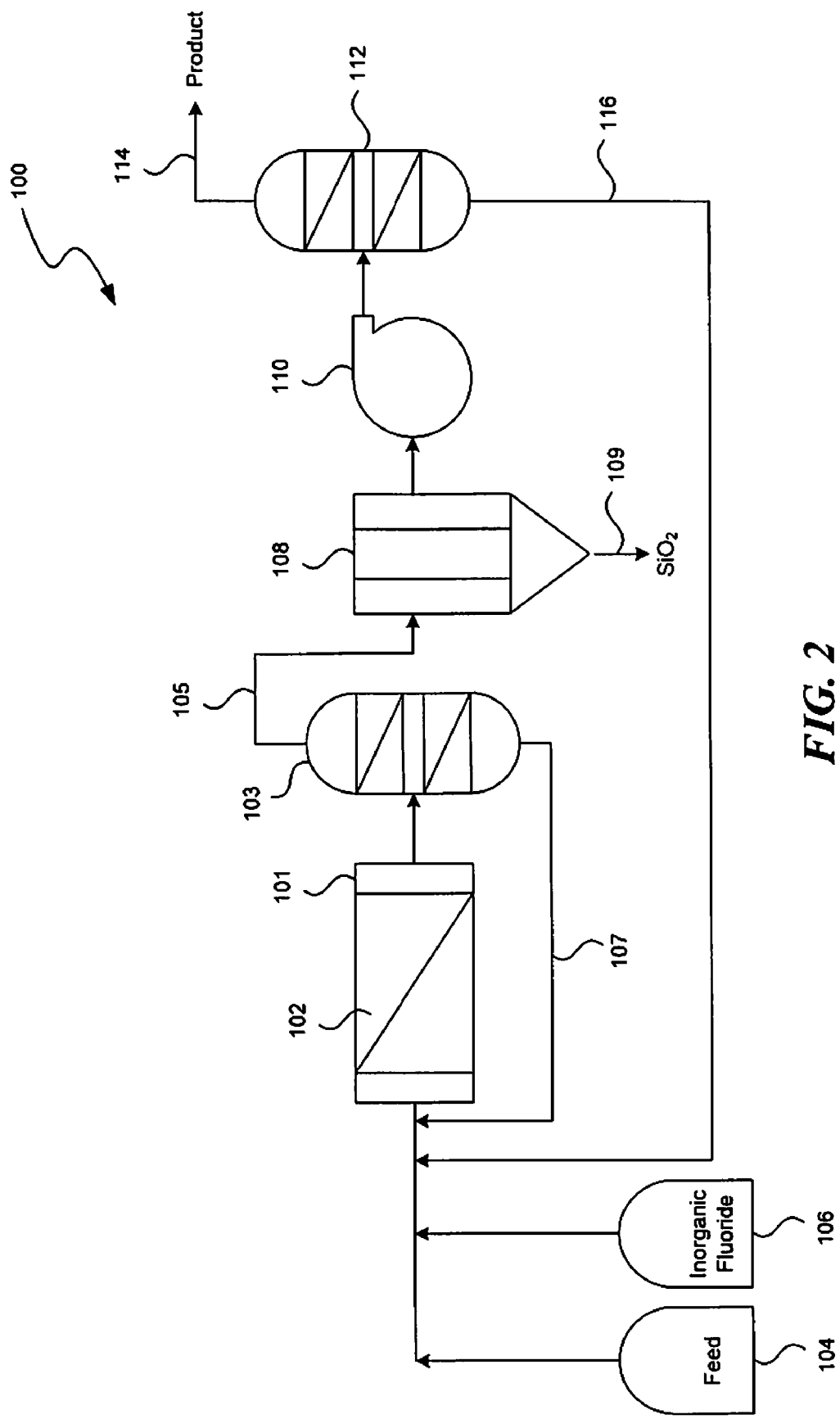
FIG. 2 is a schematic diagram illustrating a system for producing hydrohalocarbon and/or halocarbon compounds using $SiF_4$ in accordance with an embodiment of the disclosure.

FIG. 2 is a schematic diagram illustrating a system 100 for producing hydrohalocarbon and/or halocarbon compounds using $SiF_4$ in accordance with an embodiment of the disclosure. The system 100 can include a reactor 101 operatively coupled to a feed storage 104 containing an organic reactant and an inorganic fluoride storage 106 containing a fluorinating agent (e.g., $SiF_4$). The organic reactant can include a chlorine-substituted alkane (e.g., pentachloroethane, hexachloroethane, tetrachloroethane, and trichloroethane), a chlorine-substituted alkene (e.g., 1,1-dichloroethene, 1,1,2-trichloroethene, and 1,1,2,2-tetrachloroethene), a chlorine-substituted aromatic compound, an alcohol, an olefin, a carboxylic acid, an ester, an ether, a ketone, and an aldehyde, and/or other suitable staring material. The reactor 101 can be configured generally as a tubular reactor constructed from Inconel, Hastelloy, nickel, and/or other fluorine-resistant material. In some embodiments, the reactor 101 can include a catalyst bed 102 containing $SbCl_5$, $Cr_2O_3$, $AlCl_3$, and/or other suitable catalyst. In other embodiments, the catalyst bed 102 can be omitted from the reactor 101, and the catalyst (e.g., $AlCl_3$) can be fed into the reactor 101 during operation.

The system 100 can also include a first separator 103 downstream of the reactor 101. The first separator 103 can be configured to remove unreacted organic reactant starting material (e.g., pentachloroethane) and/or reaction byproducts (e.g., $SiCl_4$) from desired HFC, CFC, and/or HCFC compounds contained in the reaction product. In the illustrated embodiment, the first separator 103 includes a distillation column that can produce a first top product from a first top end 105 and a first bottom product from a first bottom end 107. The first top product can include HFC, CFC, and/or HCFC compounds contained in the reaction product. The first bottom product can include $SiCl_4$, unreacted pentachloroethane, and/or other intermediate compounds (e.g., HCFC-121), which are recycled to the reactor 101. In other embodiments, the first bottom product can also be purified, scrubbed, and/or otherwise treated to derive a useful product in addition to or in lieu of being recycled to the reactor 101.

The system 100 can also include a scrubber 108 that receives the first top product from the first separator 103. The scrubber 108 can include materials configured to remove halide impurities (e.g., silicon chlorofluorides) and/or unreacted fluorinating agent (e.g., $SiF_4$) from the first top product. For example, in one embodiment, the scrubber 108 includes a liquid base containing, e.g., potassium hydroxide (KOH), sodium hydroxide (NaOH), and/or other base for absorbing, reacting, and/or otherwise converting unreacted $SiF_4$ into siloxanes. In another embodiment, the scrubber 108 includes a solid base (e.g., pellets) containing KOH, NaOH, and/or other base. In further embodiments, the scrubber 108 can include a base in a liquid-solid form and/or other materials for removing the halide byproduct impurities and/or the unreacted fluorinating agent (e.g., $SiF_4$).

In certain embodiments, the system 100 can optionally include a pressurizing device 110 downstream of the scrubber 108 to increase the pressure of the scrubbed first top product. In certain embodiments, the pressurizing device can include a centrifugal compressor, a diaphragm compressor, a reciprocating compressor, and/or other suitable types of compressor when the first top product is at least partially a gas after passing through the scrubber 108. In other embodiments, the pressuring device can include a centrifugal pump, a positive displacement pump, and/or other suitable types of pump when the first top product is a liquid after passing through the scrubber 108. In further embodiments, the pressurizing device 110 can be omitted.

The system 100 can further include a second separator 112 downstream of the optional pressurizing device 110. The second separator 112 can be configured to split HFC, CFC, and/or HCFC compounds in the first top product. In the illustrated embodiment, the second separator 112 includes a distillation column that can produce a second top product from a second top end 114 and a second bottom product from a second bottom end 116. The second top product can include, e.g., HFC-125, and the second bottom product can include at least one of HCFC-121, HCFC-122, HCFC-123, and HCFC-124 when pentachloroethane is the starting material. In the illustrated embodiment, the second bottom product is recycled to the reactor 101. In other embodiments, the second bottom product can also be purified, scrubbed, and/or otherwise treated to derive a useful product.

In operation, the reactor 101 first receives a feed stream, also referred to as a reaction feed, containing, for example, a chlorine-substituted alkane, a chlorine-substituted alkene, a chlorine-substituted aromatic compound, an olefin, an alcohol, a carboxylic acid, an ester, an ether, a ketone, an aldehyde and/or other suitable organic reactant compound from the feed storage 104 and a fluorinating agent containing at least one inorganic fluoride (e.g., $SiF_4$) from the inorganic fluoride storage 106. In one embodiment, $SiF_4$ can be in a stoichiometric amount required to fluorinate an organic reactant compound. For example, the molar ratio of $SiF_4$ to pentachloroethane can be about 1.12:1. In other embodiments, $SiF_4$ can be in molar excess of the stoichiometric amount required to fluorinate an organic reactant compound. For example, the molar ratio of $SiF_4$ to organic reactant in the reaction feed can be from about 2:1 to about 4:1.

In the reactor 101, $SiF_4$ and the organic reactant contact the catalyst (e.g., $AlCl_3$) held in the catalyst bed 102. In certain embodiments, the reactor 101 can be configured to permit a gas-phase reaction. For example, the reactor 101 can be held at a temperature of about 200° to about 400° C. and at a pressure of about 500 to 800 psig (i.e., about 3.45 MPa to about 5.52 MPa) such that the reactants are in the gas phase. In other embodiments, the reactor 101 can be configured to permit a liquid-phase reaction. For example, the reactor 101 can be held at a temperature of about 60° to about 90° C. and at a pressure of about 50 to 100 psig (i.e., about 0.345 MPa to about 0.69 MPa) such that the reactants are in the liquid phase. In further embodiments, the reactor 101 can be configured to carry out multiphase (e.g., liquid-gas, solid-gas, liquid-solid) reactions.

Under such temperature and pressure conditions, $SiF_4$ can fluorinate the organic reactant to form HFC, CFC, and/or HCFC compounds in the presence of the catalyst. In certain embodiments, $SiF_4$ can fluorinate a chlorine-substituted alkane. For example, $SiF_4$ can react with pentachloroethane ($CHCl_2CCl_3$) to produce at least one of HCFC-121 ($CHCl_2CCl_2F$), HCFC-122 ($CF_2ClCHCl_2$), HCFC-123 ($CHCl_2CF_3$), HCFC-124 ($CHClFCF_3$), and HFC-125 ($CHF_2CF_3$) as follows:

$$SiF_4+CHCl_2CCl_3 \rightarrow CHCl_2CCl_2F+CF_2ClCHCl_2+CHCl_2CF_3+CHClFCF_3+CHF_2CF_3$$

In another example, $SiF_4$ can also be employed to fluorinate pentachloroethane ($CCl_3CCl_3$) to produce at least one of CFC-111 ($CCl_3CCl_2F$), CFC-112 ($CCl_2FCCl_2F$), CFC-113 ($CCl_2FCClF_2$), CFC-114 ($CClF_2CClF_2$), and CFC-115 ($CClF_2CF_3$) as follows:

$$SiF_4+CCl_3CCl_3 \rightarrow CCl_3CCl_2F+CCl_2FCCl_2F+CCl_2FCClF_2+CClF_2CClF_2+CClF_2CF_3$$

In yet another example, $SiF_4$ can fluorinate trichloroethane to produce at least one of HFC-143a ($CH_3CF_3$), as follows:

$$SiF_4+CH_3CCl_3 \rightarrow CH_3CF_3+CH_3CClF_2+CH_3Cl_2F$$

In other embodiments, $SiF_4$ can also fluorinate a chlorine-substituted alkene compound in the presence of a catalyst to produce unsaturated HFC, CFC, and/or HCFC compounds. For example, $SiF_4$ can fluorinate 1,1-dichloroethene ($CH_2CCl_2$) to produce at least one of 1-chloro-1-fluoroethene ($CH_2=CClF$) and 1,1-difluoroethene ($CH_2=CF_2$) as follows:

$$SiF_4+CH_2=CCl_2 \rightarrow CH_2=CClF+CH_2=CF_2$$

In another example of fluorination of an unsaturated chlorine-substituted alkene, $SiF_4$ can fluorinate 1,1,2-trichloroethene ($CHCl=CCl_2$) to produce at least one of 1,2-dichloro-2-fluoroethene ($CHCl=CClF$), 1-chloro-2,2-difluoroethene ($CHCl=CF_2$), 1-chloro-1,2-difluoroethene ($CHF=CClF$), and 1,1,2-trifluoroethene ($CHF=CF_2$) as follows:

$$SiF_4+CHCl=CCl_2 \rightarrow CHCl=CClF+CHCl=CF_2+CHF=CClF+CHF=CF_2$$

In a further example, $SiF_4$ can fluorinate 1,1,2,2-tetrachloroethene ($CCl_2=CCl_2$) to produce at least one of 1,1,2-trichloro-2-fluoroethene ($CCl_2=CClF$), 1,1-dichloro-2,2-difluoroethene ($CCl_2=CF_2$), 1,2-dichloro-1,2-difluoroethene ($CClF=CClF$), and 1,1,2,2-tetrafluoroethene ($CF_2=CF_2$) as follows:

$$SiF_4+CCl_2=CCl_2 \rightarrow CCl_2=CClF+CCl_2=CF_2+CClF=CClF+CF_2=CF_2$$

In other embodiments, SiF4 can react with a chlorine-substituted aromatic compound (e.g., trichloromethylbenzene), an alcohol (ROH), a carboxylic acid (ROOH), an ester (ROOR'), an ether (ROR'), a ketone (RCOR'), and/or an aldehyde (RC(O)H) to produce HFC, CFC, and/or HCFC compounds as follows:

$$SiF_4+C_6H_5Cl_3 \rightarrow C_6H_5F_3$$

$$SiF_4+ROH \rightarrow RF$$

$$SiF_4+RCOOH \rightarrow RCF_3$$

$$SiF_4+RCOOR' \rightarrow RCF_3$$

$$SiF_4+ROR' \rightarrow RF+R'F$$

$$SiF_4+RCOR' \rightarrow RCF_2R'$$

$$SiF_4+RC(O)H \rightarrow RCHF_2$$

where R and R' can include alkyl, alkenyl, alkynyl, or aryl groups, and R can be the same as or different than R'.

"Alkyl" groups generally refer to branched or unbranched saturated hydrocarbon groups. Examples of the alkyl groups can include methyl, ethyl, propyl, butyl, pentyl, 1-methylbutyl, 1-ethylpropyl, 3-methylpentyl, hexyl, heptyl, etc. "Alkenyl" groups generally refer to branched or unbranched hydrocarbon groups containing at least one double bond. Examples of the alkenyl groups include ethenyl, n-propenyl, isopropenyl, n-butenyl, isobutenyl, octenyl, decenyl, tetradecenyl, etc. "Alkynyl" groups generally refer to branched or unbranched hydrocarbon groups containing at least one triple bond. Examples of the alkynyl groups include ethynyl, n-propynyl, isopropynyl, n-butynyl, isobutynyl, octynyl, decynyl, etc. "Aryl" groups generally refer to one or more aromatic rings. Some aryl groups can include multiple fused aryl rings (e.g., naphthyl), and others can include multiple unfused aryl rings (e.g., biphenyl). Aryl groups may also include aryl rings fused or unfused with one or more cyclic hydrocarbon, heteroaryl, or heterocyclic rings. As used herein, the term "aryl" includes heteroaryl.

In any of the reactions discussed above, although the reactions are shown to produce multiple fluorinated molecules, in some embodiments, the reactions may produce any one of the multiple fluorinated molecules, or a combination of any number (e.g., two, three, or four) of the fluorinated molecules indicated in the reactions above. For example, in some embodiments, the reaction between pentachloroethane and $SiF_4$ can produce only HFC-125 and HCFC-124 but not the other possible fluorination products. In other embodiments, the reaction may produce only HFC-125 by, e.g., controlling the molar ratio between pentachloroethane and $SiF_4$.

The inventor has recognized that $Cr_2O_3$, $AlCl_3$, $SbCl_5$, and/or other Lewis acid catalysts and superacid catalysts can cause $SiF_4$ to readily react with chlorine-substituted alkanes, chlorine-substituted alkene, chlorine-substituted aromatic compounds, alcohols, carboxylic acids, esters, ethers, ketones, and/or aldehydes. According to conventional techniques, aluminum trichloride has been used as a catalyst to facilitate fluorination of chlorocarbons using hydrogen fluoride (HF) as the fluorinating agent. Without being bound by theory, it is believed that an equilibrium among species of $AlCl_xF_y$ (x+y=3) exist in such fluorination reactions as follows:

$$AlCl_3 \leftrightarrow AlCl_2F \leftrightarrow AlClF_2 \leftrightarrow AlF_3$$

However, the reaction mechanisms and kinetics for different starting reagents and/or the species and ratios of final products may be unpredictable as discovered by Schumb et al. (See Schumb, W. C.; Breck, D. W., *In Some Metathetical Reactions of the Gaseous Fluorides of Group IV*, J. Am. Chem. Soc. 1951, 74, 1754-1760,) the disclosure of which is incorporated herein in its entirety.

Without being bound by theory, in accordance with several embodiments of the present invention, it is believed that SiF4 first reacts with the catalyst (e.g., AlCl3) to form a series of equilibria among species of $AlCl_xF_y$ (x+y=3) and those of $SiCl_xF_y$ (x+y=4) as follows:

$$AlCl_3 + SiF_4 \leftrightarrow AlCl_2F + SiF_3Cl \leftrightarrow AlClF_2 + SiF_2Cl_2 \leftrightarrow AlF_3 + SiFCl_3$$

As shown above, a first equilibrium among species of $AlCl_xF_y$ (x+y=3) and a second equilibrium among species of $SiCl_xF_y$ (x+y=4) exist concurrently in several embodiments of the present invention. Surprisingly, the inventor has discovered that the first and second co-existing equilibria have favorable critical equilibrium for achieving fluorination of chlorocarbons facilitated by the $AlCl_xF_y$ (x+y=3) system.

The inventor also discovered that the $SiCl_4$ content of the $SiCl_xF_y$ mixture is believed to affect the resulting fluorinated products and is dependent on the reaction temperature, the reaction pressure, and the $SiF_4/AlCl_3$ molar ratio as shown in the table below:

| Temperature (° C.) | SiF$_4$/AlCl$_3$ ratio | Pressure (psig) | % SiCl$_4$ in SiCl$_x$F$_y$ |
| --- | --- | --- | --- |
| 195-250 | 1.2 | 103 (start) → 1 (end) | 76 |
| 195-250 | 0.6 | 115 (start) → 1 (end) | 100 |
| 250 | 1.24 | 1 (start → end) | 23 |
| 500 | 1.15 | 1 (start → end) | 75 |

It is believed that the $AlCl_xF_y$ (x+y=3) compounds may then act as super Lewis acid catalysts to lower the activation energy for fluorinating the organic reactant. The super Lewis acid is believed to remove fluoride ions from SiF$_4$ to promote fluorination of chlorocarbons and/or other organic reactants. It is also believed that AlF$_3$ is a more efficient catalyst than AlCl$_2$F and/or AlClF$_2$. Thus, in some embodiments, the balance of the reaction equilibria can be shifted toward AlF$_3$ by, for example, selecting at least one of the reaction temperature, the reaction pressure, and the SiF$_4$/AlCl$_3$ molar ratio by adding/reducing excess SiF$_4$ to the reaction feed, removing products from the reaction, and/or using other suitable techniques.

In one embodiment, the reaction described above can be carried out in a batch mode. For example, the reaction conditions can be maintained in the reactor 101 until the reaction is complete, and then the reaction product can be discharged from the reactor 101 to the first separator 103. In other embodiments, the reaction described above can be carried out in a continuous mode. For example, the reactor 101 can be configured as a plug-flow reactor, a constantly stirred tank reactor, and/or other types of reactor with sufficient residence time to allow the completion of the reaction in a continuous mode.

After reacting in the reactor 101, the reaction product flows from the reactor 101 to the first separator 103 for removing any unreacted organic reactant (e.g., pentachloroethane) and/or reaction byproducts (e.g., SiCl$_4$ and SiCl$_x$F$_y$ (x+y=4)) from desired HFC, CFC, and/or HCFC compounds in the reaction product. For example, when the organic reactant contains pentachloroethane, the reaction product can be distilled at the first separator 103. The distillation can produce the first bottom product containing at least one of SiCl$_4$, HCFC-121, and unreacted pentachloroethane and the first top product containing at least one of SiF$_4$, SiClF$_3$, SiCl$_2$F$_2$, SiCl$_3$F, HCFC-122, HCFC-123, HCFC-124, and HFC-125. The first bottom product can then be recycled to the reactor 101. The first separator 103 can operate at a pressure of about 110 psig (0.758 MPa) to about 170 psig (1.172 MPa) and a temperature of about 20° to about 40° C.

The first top product then flows to the scrubber 108 for removing excess SiF$_4$ and any produced SiCl$_x$F$_y$ (x+y=4) compounds. In one embodiment, the scrubber 108 can contain KOH and/or NaOH that reacts with the excess SiF$_4$ and SiCl$_x$F$_y$ (x+y=4) compounds to produce SiO$_2$ in order to purify the reaction product. In other embodiments, the scrubber 108 can remove the excess SiF$_4$ and SiCl$_x$F$_y$ (x+y=4) compounds using other physical and/or chemical techniques.

In certain embodiments, the first top product can be optionally pressurized after excess SiF$_4$ and any produced SiCl$_x$F$_y$ (x+y=4) compounds are scrubbed. For example, the pressurizing device 110 can increase the pressure of the first top product to a pressure of about 35 psig (0.24 MPa) to about 300 psig (2.068 MPa). In other embodiments, the first top product can be depressurized before flowing to the second separator 112.

The second separator 112 then splits the produced HFC, CFC, and/or HCFC compounds in the first top product to produce the second top product (containing essentially of a desired product, e.g., HFC-125) from the second top end 114 and the second bottom product containing other HFC, CFC, and/or HCFC compounds (e.g., HCFC-121, HCFC-122, HCFC-123, and HCFC-124) from the second bottom end 116. The HFC, CFC, and/or HCFC compounds in the second bottom product can then be recycled to the reactor 101. The second separator 112 can operate at a pressure of about 35 psig (0.24 MPa) to about 300 psig (2.068 MPa) and a temperature of about −25° to about 45° C.

Fluorination reactions carried out in the system 100 described above can efficiently and cost-effectively produce hydrohalocarbon and/or halocarbon compounds. For example, unlike conventional techniques having multiple processing steps, in some embodiments, using the system 100 can produce desired hydrofluorocarbon compounds in one reaction step via direct chlorine-fluorine exchange on the organic reactant (e.g., hydrochlorocarbon compounds). The reaction has been observed to produce an unexpectedly high yield of conversion from hydrochlorocarbon compounds. For example, when pentachloroethane is used as the starting material, at least about 80%, more preferably at least about 82%, and even more preferably at least about 86% of pentachloroethane in the starting material has been converted.

The system 100 can also produce desired HFC, CFC, and/or HCFC compounds with reduced operating cost because the production cost for $SiF_4$ is relatively lower than other fluorinating agents (e.g., $GeF_4$, HF, etc.) $SiF_4$ is typically produced from $SiO_2$ commonly contained in sand and uranium tetrafluoride (UF4) in a fluorine extraction process. There is a virtually limitless supply of $SiO_2$ and a significant amount of $UF_4$ held in storage as waste in the United States. As a result, the cost for the producing $SiF_4$ can be lower than using other fluorinating agents because of raw material cost. Accordingly, the system 100 can have a lowered operating cost because raw material cost is a major operational expenditure.

Moreover, the system 100 can produce desired HFC, CFC, and/or HCFC compounds with reduced purification cost. According to conventional techniques, HF is typically used as the fluorinating agent to react with a reactant in a combination of chlorination and hydrofluorination reactions. Such reactions can generate many unwanted CFC byproducts, which must be removed from the desired product. It is believed that using $SiF_4$ as the fluorinating agent can eliminate at least some of these CFC byproducts, and thus reduce the purification cost of the desired product.

In the system 100 described above, in certain embodiments, the first and/or second separators 103, 112 can also include a flash tank, a cyclone, and/or other liquid-liquid separation/liquid-gas separation devices in addition to or in lieu of the distillation columns. Further, although the first and second bottom products are described above as being recycled to the reactor 101, in some embodiments, at least one of the first and second bottom products can be diverted from the reactor 101 for further processing. In further embodiments, the system 100 can operate in a one-pass mode without any recycling to the reactor 101. Moreover, the system 100 can have other process configurations with additional and/or different processing devices. For example, in some embodiments, the system 100 can include product traps for capturing desired compounds from the reaction product.

Method for Producing Hydrohalocarbon and/or Halocarbon Compounds

Figure 3:
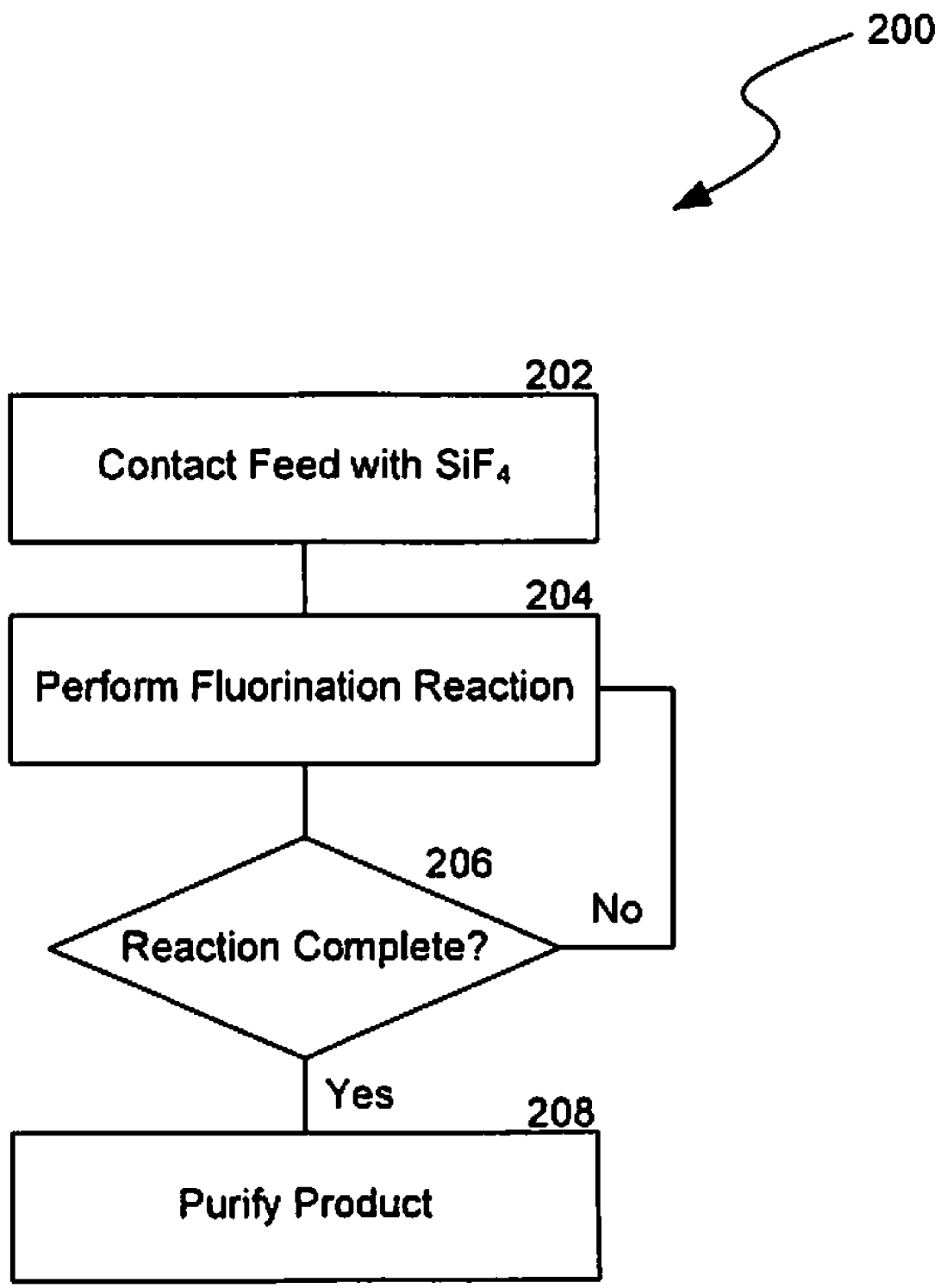
FIG. 3 is a flow chart illustrating a method for producing hydrohalocarbon and/or halocarbon compounds using $SiF_4$ in accordance with an embodiment of the disclosure.

FIG. 3 is a flow chart illustrating a method 200 for producing hydrohalocarbon and/or halocarbon compounds in accordance with an embodiment of the disclosure. The method 200 can include contacting a reaction feed containing a reactant to be fluorinated with $SiF_4$ in the presence of a catalyst (e.g., $SbCl_5$, $AlCl_3$, and/or other suitable superacids and/or Lewis acids) at block 202. Suitable organic reactants can include chlorine-substituted alkanes (e.g., pentachloroethane, hexachloroethane, trichloroethane, etc.), chlorine-substituted alkenes (1,1-dichloroethene, 1,1,2-trichloroethene, 1,1,2,2-tetrachloroethene, etc.), chlorine-substituted aromatic compounds, alcohols, carboxylic acids, esters, ethers, ketones, aldehydes, among others. The molar ratio of catalyst/reactant/$SiF_4$ can be about 1:A:B (2<A<15 and 4<B<60).

The method 200 then includes performing fluorination reaction on the organic reactant at block 204 to produce HFC, CFC, and/or HCFC compounds. Suitable reaction temperatures can be about 200° to about 400° C. for gas phase reactions, and about 60° to about 90° C. for liquid phase reactions. Suitable pressures can be about 500 to 800 psig. Under such conditions, in some embodiments, a fluorine-chlorine exchange can be performed on the organic reactant containing, e.g., chlorocarbon compounds. In other embodiments, the organic reactant can be fluorinated by substituting other atoms (e.g., oxygen) on the organic reactant.

A decision is made at block 206 to determine whether the reaction is complete. In one embodiment, the decision can be based on a reaction time (e.g., 6-8 hours). In another embodiment, the decision can be based on a conversion of the reactant and/or other reaction parameters. For example, an operator can periodically sample the material in the reactor 101 to determine a concentration of the organic reactant contained in the starting material. If the concentration of the organic reactant is below a certain threshold, then the reaction is indicated to be complete.

If the reaction is complete, the method 200 further includes purifying the reaction product at block 208. Purifying the reaction product can include separating the desired HFC, CFC, and/or HCFC compounds from the reaction product using condensation, distillation, liquid-liquid extraction, liquid-gas separation, and/or other suitable separation techniques. If the reaction is not complete, the process reverts to performing the fluorination reaction on the organic reactant, e.g., pentachloroethane, at block 204.

EXAMPLES

Figure 4:
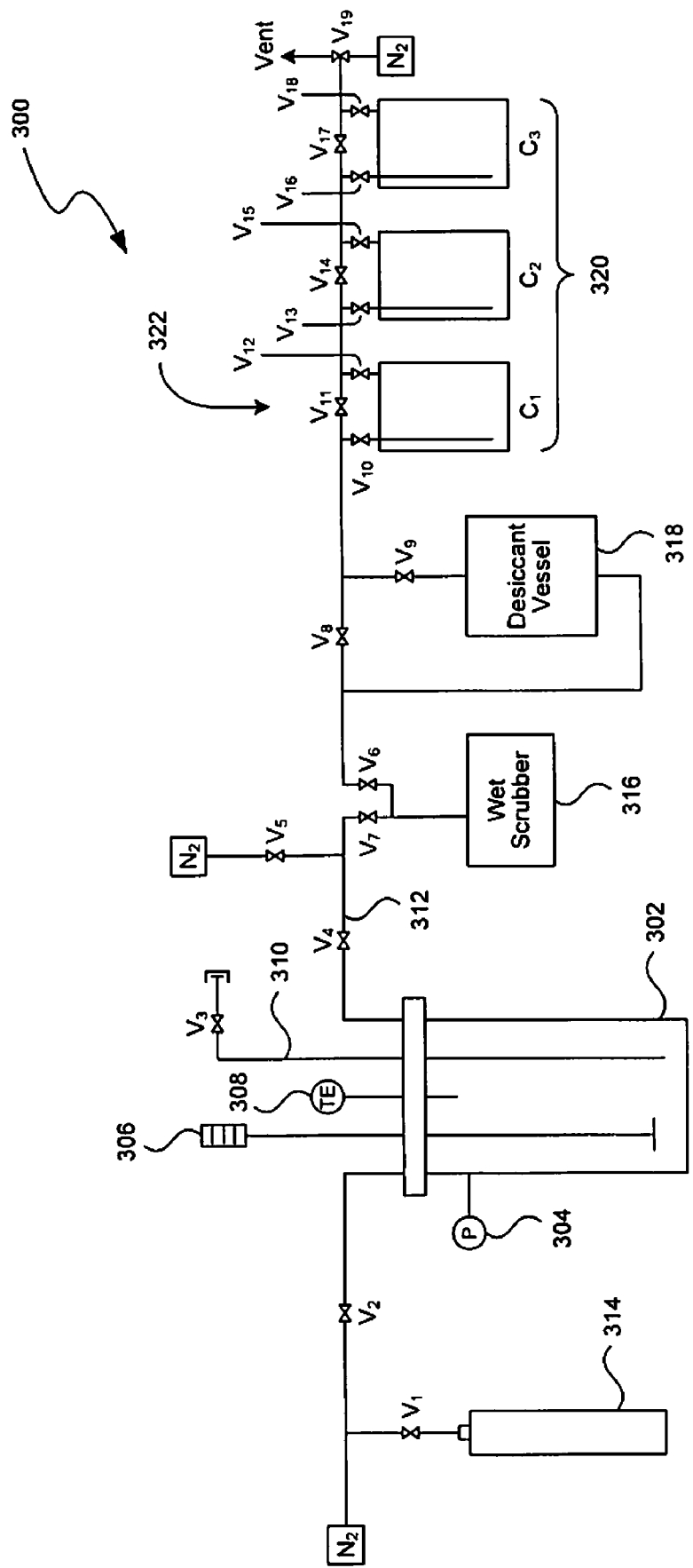
FIG. 4 is a schematic diagram illustrating a system for producing hydrohalocarbon and/or halocarbon compounds using $SiF_4$ in accordance with an embodiment of the disclosure.

Experiments were conducted to fluorinate an illustrative organic reactant starting material, e.g., pentachloroethane, using $SiF_4$ in the presence of a catalyst (e.g., $AlCl_3$) in a bench-top reactor (Model No. 4563) supplied by the Parr Instrument Company of Moline, Illinois. FIG. 4 is a schematic diagram illustrating an experimental system 300 for producing HFC-125 in accordance with an embodiment of the disclosure. As shown in FIG. 4, the system 300 includes an Inconel 600 reactor 302 having a volume of about 600 mL. The reactor 302 includes a pressure monitor 304, a mixer 306, and a temperature monitor 308. The reactor 302 also includes a liquid sample line 310 and a gas sample line 312. The system 300 also includes a cylinder 314 holding gaseous $SiF_4$. The system 300 also includes a 200 mL wet scrubber 316 containing KOH and a desiccant vessel 318 containing $Al_2O_3$ and KOH pellets. The system 300 further includes three 75 mL sampling cylinders 320 (labeled C1-C3). The sampling cylinders 320 can be held at various temperatures and pressures for collecting materials with different boiling points. Various components of the system 300 can be isolated using a plurality of valves 322 (labeled V1-V19).

Fourier transform infrared (FTIR) spectra were recorded on a MIDAC I1201 bench-top infrared spectrometer as neat liquids between potassium bromide (KBr) plates or gas samples in a 10 cm path-length demountable gas cell with zinc-selenium (ZnSe) windows. $^1H$, $^{13}C$, and $^{19}F$ NMR spectra were obtained on a 300 MHz Bruker AMX spectrometer at 200, 50, and 188 MHz, respectively, by using $CDCl_3$ as a locking solvent. Chemical shifts were reported relative to $Me_4Si$ or $CFCl_3$. GC-MS spectra were obtained with a Shimadzu Q5050 spectrometer (El-mode). Elemental analyses were performed by the Desert Analytics Laboratory of Tucson, Arizona.

Liquid pentachloroethane (25.8 g, 0.127 mol) and solid aluminum chloride (4.0 g, 0.030 mol, Bp 194° C.) were charged into the reactor 302. The reactor 302 was closed and bolted. Silicon tetrafluoride (27.7 g, 0.267 mol) was fed into the reactor 302 at 22° C. in a vented hood. The pressure in the reactor 302 was 150 psig. The gas-in and gas-out valves on the reactor 302 were closed to isolate the reagents in the reactor 302 while the supply sample line was purged several times and then disconnected. The reactor 302 was then transferred to a heating mantle and connected to a manifold with the scrubber 316, the desiccant vessel 318 and sample cylinders 320 for cryogenic distillation. The heater warmed the stirred reagents at 340° C. The reactor pressure rose to 515 psig at 340° C. After 8 hours, the reactor 302 was slowly cooled to room temperature, and the reactor pressure dropped to 202 psig at 22° C. It is believed that most silicon based byproducts, i.e. $SiClF_3$ (Bp, −70° C.), $SiCl_2F_2$ (Bp, −32° C.) and $SiCl_3F$ (Bp, 12° C.), were volatile at 22° C. The gaseous chlorofluorosilanes and unreacted $SiF_4$ were vented through the gas-out valve to the solution in the 200 mL 8 M KOH scrubber 316 until the pressure in the reactor 302 dropped to 0 psig. Subsequently, the reactor 302 was pressurized three times with nitrogen to 90 psig and vented through the scrubber 316. The gaseous reaction product was collected in a 75 mL sample cylinder that was cooled to −196° C. with liquid nitrogen. The crude product was subsequently separated by cryogenic distillation and the components identified by comparing their FTIR spectra with appropriate literature references.

The reaction had a conversion of about 86% pentachloroethane to a gaseous product, which was identified as a mixture of 80% HFC-125 (Bp −48° C.) and 20% HCFC-124 (Bp −10° C). The total gas pressure in the 75 cc cylinder was 90 psig indicating about 30% product collection. On opening the reactor 302, some 3.6 g of unreacted liquid pentachloroethane was recovered along with solid and dark brown aluminum trifluoride in the reactor 302. Gaseous chlorofluorosilanes, i.e., $SiClF_3$, $SiCl_2F_2$, and $SiCl_3F$, were obtained. There was no evidence of fuming $SiCl_4$ in the reaction product, thus indicating that as much as about 20 g of the starting pentachloroethane was converted. The selectivity of the reaction in forming HFC-125 and HCFC-124 was about 60%:40% based on FTIR data.

From the foregoing, it will be appreciated that specific embodiments of the invention have been described herein for purposes of illustration, but that various modifications may be made without deviating from the invention. Elements of one embodiment may be combined with other embodiments in addition to or in lieu of the elements of the other embodiments. Accordingly, the invention is not limited except as by the appended claims.

I claim:

1. A method for fluorinating an organic reactant, comprising: reacting an organic reactant selected from the group consisting of a chlorine-substituted alkane, a chlorine-substituted alkene, a chlorine-substituted aromatic compound, an alcohol, a carboxylic acid, an ester, an ether, a ketone, and an aldehyde with silicon tetrafluoride ($SiF_4$) in the presence of a metal halide catalyst under conditions effective to form a fluorinated organic product, wherein reacting the organic reactant with silicon tetrafluoride includes reacting at least one of 1,1,1,2,2-pentachlorethane, 1,1,1,2,2,2-hexachlorethane, 1,1,1-trichlorethane, and 1,1,2,2-tetrachlorethane with silicon tetrafluoride in the presence of aluminum trichloride.

2. A method for fluorinating an organic reactant, comprising:
reacting an organic reactant with silicon tetrafluoride ($SiF_4$) in the presence of an aluminum trichloride catalyst, the organic reactant being selected from the group consisting of 1,1,1,2,2-pentachlorethane, 1,1,1,2,2,2-hexachlorethane, 1,1,1-trichlorethane, and 1,1,2,2-tetrachlorethane, 1,1-dichloroethene, 1,1,2-trichloroethene, and 1,1,2,2-tetrachloroethene;
concurrently forming a series of equilibria between species of $AlCl_xF_y$ (x+y=3) and species of $SiCl_aF_b$ (a+b=4), as follows:

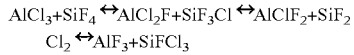

fluorinating the organic reactant with silicon tetrafluoride while catalyzed by the species of $AlCl_xF_y$ (x+y=3) under conditions effective to form a fluorinated organic product.

3. The method of claim 1 wherein reacting an organic reactant with silicon tetrafluoride includes reacting the organic reactant with silicon tetrafluoride in the presence of aluminum trichloride at a temperature of about 200°-400° C. or about 60° C.-90° C.

4. The method of claim 1 wherein reacting an organic reactant with silicon tetrafluoride includes reacting the organic reactant with silicon tetrafluoride in the presence of aluminum trichloride at a pressure of about 500 to 800 psig.

5. The method of claim 1 wherein reacting an organic reactant with silicon tetrafluoride includes reacting the organic reactant with silicon tetrafluoride at a molar ratio of silicon tetrafluoride to aluminum trichloride of about 2 to about 15.

6. The method of claim 1 wherein reacting an organic reactant with silicon tetrafluoride includes reacting the organic reactant with silicon tetrafluoride at a molar ratio of silicon tetrafluoride to aluminum trichloride of about 1 to about 4.

7. The method of claim 1 wherein reacting an organic reactant with silicon tetrafluoride includes reacting the organic reactant with silicon tetrafluoride in a gas phase reaction.

8. The method of claim 1 wherein reacting an organic reactant with silicon tetrafluoride includes reacting the organic reactant with silicon tetrafluoride in a liquid phase reaction.

9. The method of claim 2, further comprising:
shifting a balance between the first and second equilibria to have a critical equilibrium for fluorinating the organic reactant with silicon tetrafluoride while catalyzed by the species of $AlCl_xF_y$ (x+y=3).

10. The method of claim 2, further comprising:
selecting at least one of a reaction temperature, a reaction pressure, and a molar ratio between the aluminum trichloride and the silicon tetrafluoride to have a critical equilibrium between the first and second equilibria for fluorinating the organic reactant with silicon tetrafluoride while catalyzed by the species of $AlCl_xF_y$ (x+y=3).

11. The method of claim 2, further comprising:
controlling a balance between the first and second equilibria to have a critical equilibrium for fluorinating the organic reactant with silicon tetrafluoride while catalyzed by the species of $AlCl_xF_y$ (x+y=3) to selectively produce the fluorinated organic product.

* * * * *